(12) United States Patent
Schattenburg et al.

(10) Patent No.: US 9,612,534 B2
(45) Date of Patent: Apr. 4, 2017

(54) EXPOSURE DOSE HOMOGENIZATION THROUGH ROTATION, TRANSLATION, AND VARIABLE PROCESSING CONDITIONS

(71) Applicant: Tokyo Electron Limited, Minato-ku, Tokyo (JP)

(72) Inventors: Mark L. Schattenburg, Framingham, MA (US); Rudolf H. Hendel, Summit, NJ (US); Michael Carcasi, Austin, TX (US)

(73) Assignee: TOKYO ELECTRON LIMITED, Tokyo (JP)

( * ) Notice: Subject to any disclaimer, the term of this patent is extended or adjusted under 35 U.S.C. 154(b) by 76 days.

(21) Appl. No.: 14/801,703

(22) Filed: Jul. 16, 2015

(65) Prior Publication Data

US 2016/0291474 A1   Oct. 6, 2016

Related U.S. Application Data

(60) Provisional application No. 62/141,003, filed on Mar. 31, 2015.

(51) Int. Cl.
*G03F 7/20* (2006.01)
*C07K 14/47* (2006.01)

(52) U.S. Cl.
CPC ............ *G03F 7/2004* (2013.01); *C07K 14/47* (2013.01)

(58) Field of Classification Search
CPC .. G03F 7/2004; G07K 14/47; G01N 33/6896; G01N 2800/28; G01N 2333/47
See application file for complete search history.

(56) References Cited

U.S. PATENT DOCUMENTS

| 4,890,309 A * | 12/1989 | Smith | G03F 1/22 250/505.1 |
|---|---|---|---|
| 6,524,755 B2 * | 2/2003 | Jin | G03F 1/32 428/408 |
| 6,653,641 B2 | 11/2003 | Lyons et al. | |
| 6,900,880 B2 | 5/2005 | Kida et al. | |

(Continued)

FOREIGN PATENT DOCUMENTS

| JP | 2002-025893 | 1/2002 |
|---|---|---|
| TW | 2014-13400 | 4/2014 |

OTHER PUBLICATIONS

International Search Report issued in PCT/US2016/021771 dated May 31, 2016.

(Continued)

*Primary Examiner* — Tony Ko
(74) *Attorney, Agent, or Firm* — DLA Piper LLP US

(57) ABSTRACT

A substrate may be disposed on a substrate support in a flood exposure treatment system. A flood exposure dose profile may be selected. The substrate may be exposed to flood irradiation from a source, and the flood irradiation may be terminated when the selected flood exposure dose profile is achieved. Exposing the substrate to flood irradiation may comprise controlling at least one of a substrate rotation rate, a source scanning rate, a substrate scanning rate, a source power setting, a distance from the source to the substrate, a source aperture setting, an angle of incidence of flood irradiation on the substrate, and a source focus position to achieve the selected flood exposure dose profile.

20 Claims, 19 Drawing Sheets

(56) References Cited

U.S. PATENT DOCUMENTS

| | | |
|---|---|---|
| 7,067,822 B2 | 6/2006 | Lyons et al. |
| 7,442,937 B2 | 10/2008 | Tsuchiya et al. |
| 7,498,590 B2 | 3/2009 | Dzengeleski |
| 7,709,818 B2 | 5/2010 | Matsuda et al. |
| 8,321,179 B2 | 11/2012 | Simon et al. |
| 9,335,638 B2 | 5/2016 | De Jager et al. |
| 2001/0042841 A1 | 11/2001 | Lyons et al. |
| 2002/0003216 A1 | 1/2002 | Kida et al. |
| 2004/0036849 A1 | 2/2004 | Kida et al. |
| 2004/0113094 A1 | 6/2004 | Lyons et al. |
| 2006/0065836 A1 | 3/2006 | Tsuchiya et al. |
| 2006/0076515 A1 | 4/2006 | Matsuda et al. |
| 2008/0029705 A1 | 2/2008 | Tsuchiya et al. |
| 2008/0073575 A1 | 3/2008 | Dzengeleski |
| 2010/0171047 A1 | 7/2010 | Matsuda et al. |
| 2011/0022360 A1 | 1/2011 | Simon et al. |

OTHER PUBLICATIONS

Written Opinion issued in PCT/US2016/021771 dated May 31, 2016.
English Language Abstract of JP 2002-025893 published on Jan. 25, 2002.
Taiwanese Office Action (with English Translation) issued in TW 105109612 dated Nov. 28, 2016.
English Language Abstract and English Language Translation of TW 2014-13400 published Apr. 1, 2014.

* cited by examiner

UV Source Options

| Source | Power | Pulse rate | Wave-length (nm) | Band (nm) | Stability | Beam Size | Cost | Size | Comment |
|---|---|---|---|---|---|---|---|---|---|
| Excimer | High (>1000 W) | 0.5-6 kHz | 308,351 | <1 | 2% pulse-pulse | <1 cm | 100K+ | large | Poor wavelength match. Can remote source. |
| Nitrogen Laser | Mid (W) | yes | 337 | <1 | ? | mm | - | large | Research only |
| HeCd or Ar+ Ion Laser | Low (mW to W) | CW | 325, 333.6, 351 | <1 | <1% | mm | 100K+ | large | Low power. Limited tube life. |
| Solid State Laser (YAG) | Mid (0.2-10W) | CW or Pulsed | 266, 355 | <1 | <1% | mm | 100K+ | Large | Low power |
| Diode Laser | Low (mW) | CW | 375 | <1 | <1% | mm | 1-10K | Small | Low power |
| Arc Lamp | Low (mW) | CW | white | any (DCF) | >1% | cm | 10K | small | Low power. Limited bulb life. Poor stability |
| Laser pulse Lamp | Mid (1W) | 10kHz | white | any (DCF) | good | 0.2 mm | 20K | small | Long lifetime |
| Micro-wave Lamp | High (>100 W) | CW | white | any (DCF) | good | 1x25 cm | 20K | small | Easy maintenance. High heat load. |
| LED Array | Mid (W) | CW or pulsed | selectable | 20 nm | <1% | 30x30 cm | 100K+ | mid | Efficient. Good potential but not ready. Large beam. |

DCF (di-chroic filter)

FIG. 1
PRIOR ART $$\text{③} \quad V_{ls} = \frac{r_{ls}^2}{2R_{wafer}\, t_{dwell}} \quad \text{or} \quad \frac{\langle \text{Light Spot Area}\rangle}{2\pi R t} \qquad \text{Light Spot Velocity}$$

$$t_{TOTAL} = \int_{R_{start}}^{R_{end}} \frac{1}{V_{ls}}\, dR + \frac{R_{start}}{V_{center}}$$

$$t_{TOTAL} = \frac{t_{dwell}}{r_{ls}^2}\left(R_{end}^2 - R_{start}^2\right) + \frac{R_{start}}{V_{center}}$$

Total scan time including the move from center $$\text{②} \quad t_{dwell} = \frac{\text{①}\left(t_{TOTAL} - \dfrac{R_{start}}{V_{center}}\right) r_{ls}^2}{\left(R_{end}^2 - R_{start}^2\right)}$$

Dwell Time, given total scan time and move from center

EXPOSURE DOSE HOMOGENIZATION THROUGH ROTATION, TRANSLATION, AND VARIABLE PROCESSING CONDITIONS

CROSS-REFERENCE TO RELATED APPLICATION

This disclosure claims priority from U.S. Provisional Application No. 62/141,003, entitled "High Power UV Flood Exposure Dose Homogenization by Combination of Rotation, Translation and Variable Processing Conditions" and filed Mar. 31, 2015, the entirety of which is incorporated by reference herein.

BACKGROUND

Substrate processing often involves exposing a substrate wafer to radiation. For example, a substrate may be exposed to ultraviolet (UV) light, including high power UV radiation. Substrates may be exposed to high power light (e.g., UV light), for example during a photolithography process and/or other manufacturing processes. Exposing an entire substrate to a substantially uniform intensity light source may ensure that the entire substrate is treated similarly at all locations, for example to ensure consistency in a photolithography operation across the entire substrate. However, broadband and/or narrower band high power UV flood source options or any exposure source may have significant dose non-uniformity across an exposed area and through time. High power UV flood exposure source or other source design and/or selection may be subject to several considerations in semiconductor processing. For example, considerations may include the following:
1. Throughput: a combination of power and exposure method (e.g., whole wafer, rastering spot, etc.)
2. Intensity versus wavelength (e.g., when process absorbance is over a narrow wavelength range)
3. Dose uniformity from source in exposed area (e.g., non-uniformity can be >5% and sometimes >10% in some systems)
4. Dose control through time
5. Cost trade-offs for throughput and uniformity considerations.

Many low cost, high power UV flood options suffer from significant dose non-uniformity across the exposed area (e.g., non-uniformity can be >5% and sometimes >10%). Many of the same low cost, high power UV flood options also suffer from drifting average power through time.

Some high power UV source examples are shown in table 100 of FIG. 1. In some sources, a microwave powered UV lamp, such as those provided by Nordson, or an LED array may be used, for example. The microwave power lamp source may use 6" or 10" bulbs that create a light bar of some desired intensity. However, the light bar may have significant intensity fall-off FIG. 2 is a sample UV intensity map 200. As shown in this example map 200, intensity may be greatest near the center of the UV lamp and may fall off towards the lamp edges. This map 200 is one example, but UV sources may have different intensity distributions based on variables such as source type, source age, presence of manufacturing defects, etc.

At times, it may be desirable to achieve a non-uniform predetermined exposure.

SUMMARY OF THE DISCLOSURE

Systems and methods described herein relate to a radiation exposure process to achieve a selected flood exposure dose profile. For example, dosing may be performed with high exposure dose (>1 J/cm$^2$) UV flood exposure processes or other substrate processing exposure types. The systems and methods described herein may use one or more of rotation, translation, and variable processing conditions to increase processing uniformity or achieve a selected dose profile of sources such as non-uniform high power UV flood exposure sources (e.g., yielding final non-uniformity of <0.5% or lower) or any other exposure source. The systems and methods described herein may further employ in-situ photo-sensor hardware that may allow real-time mapping of source average power and across-source non-uniformity that may be used in advanced process control schemes. Dose homogenization may be used for many potential radiation sources, such as the examples shown in table 100 of FIG. 1.

In an example embodiment, a substrate may be disposed on a substrate support in a flood exposure treatment system. A flood exposure dose profile may be selected. The substrate may be exposed to flood irradiation from a source, and the flood irradiation may be terminated when the selected flood exposure dose profile is achieved. Exposing the substrate to flood irradiation may comprise controlling at least one of a substrate rotation rate, a source scanning rate, a substrate scanning rate, a source power setting, a distance from the source to the substrate, a source aperture setting, an angle of incidence of flood irradiation on the substrate, and a source focus position to achieve the selected flood exposure dose profile.

While the systems and methods described herein are discussed in the context of high power UV processes to achieve a uniform dose profile, the selectable dose profile concepts provided may be used for any radiation-based process with inherent source non-uniformities. The systems and methods described herein may be used with a single source system and/or may be applied to the unified intensity signature of multiple sources (e.g., multiple lamps).

BRIEF DESCRIPTION OF THE DRAWINGS

FIG. 1 is a table of light source options.

FIG. 18 is a set of equations for a circular light spot shape according to an embodiment of the invention.

DETAILED DESCRIPTION OF SEVERAL EMBODIMENTS

Figure 3:
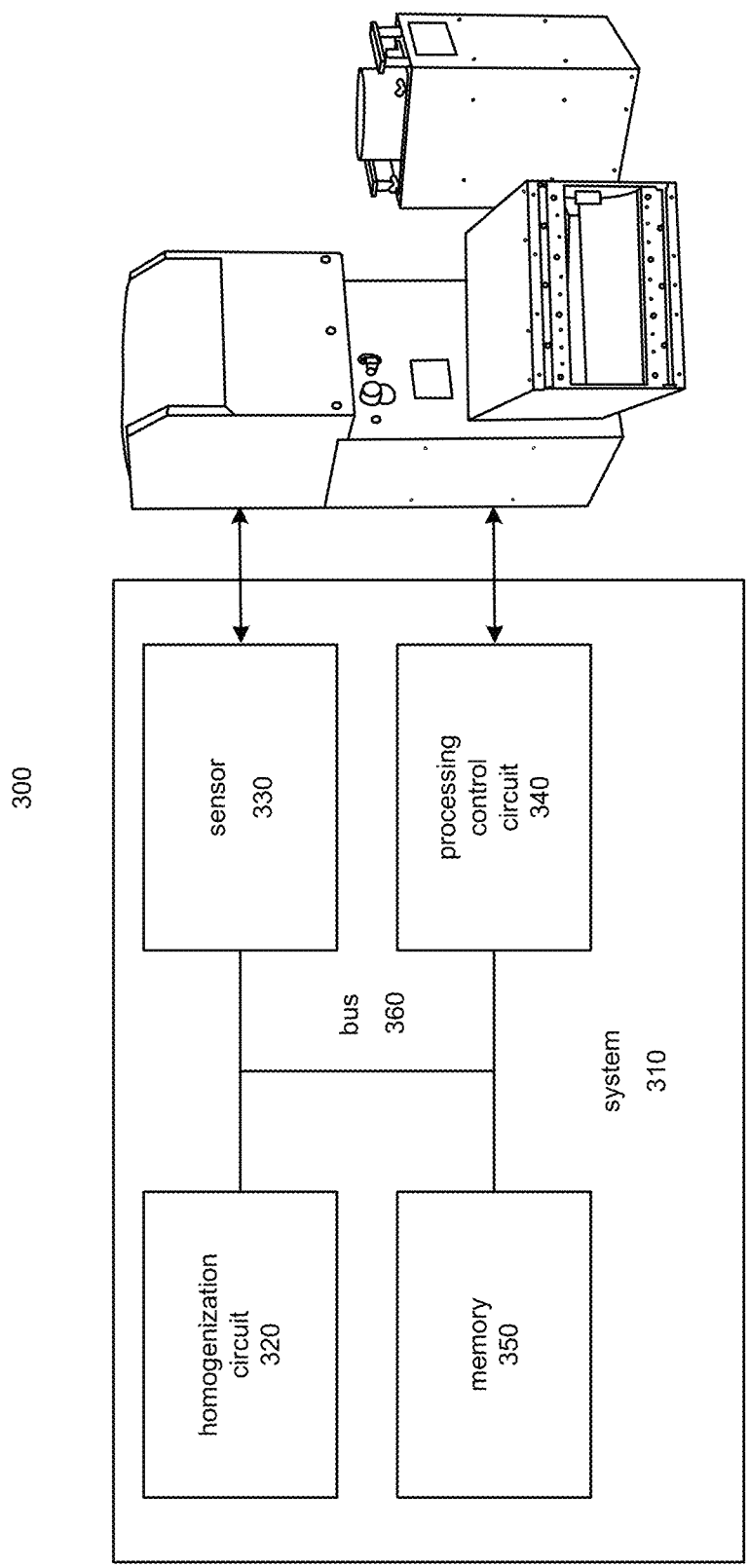
FIG. 3 is a dose homogenization system according to an embodiment of the invention.

FIG. 3 is a dose homogenization system 310 for use with a UV source 300 according to an embodiment of the invention. The system 310 may include one or more processing circuits (e.g., homogenization circuit 320 and/or processing control circuit 340), one or more sensors 330, memory 350, and/or other elements. Sensors 330 may measure UV source 300 lamp intensity and fall-off. Homogenization circuit 320 may determine UV source 300 system settings to optimize UV light dosing homogeneity. Processing control circuit 340 may control elements of the UV source 300 (e.g., motors, UV light, etc.) to implement the determined UV optimization. Functions and features of these elements 320-350 are described in greater detail below. These elements 320-350 may be interconnected via a bus 360. Some elements may be combined (e.g., a single processing circuit may perform homogenization circuit 320 and processing control circuit 340 functions in some embodiments). In some embodiments, elements such as the homogenization circuit 320 and/or processing control circuit 340 may be special purpose circuits constructed and arranged to perform the functions described below.

Figure 4:
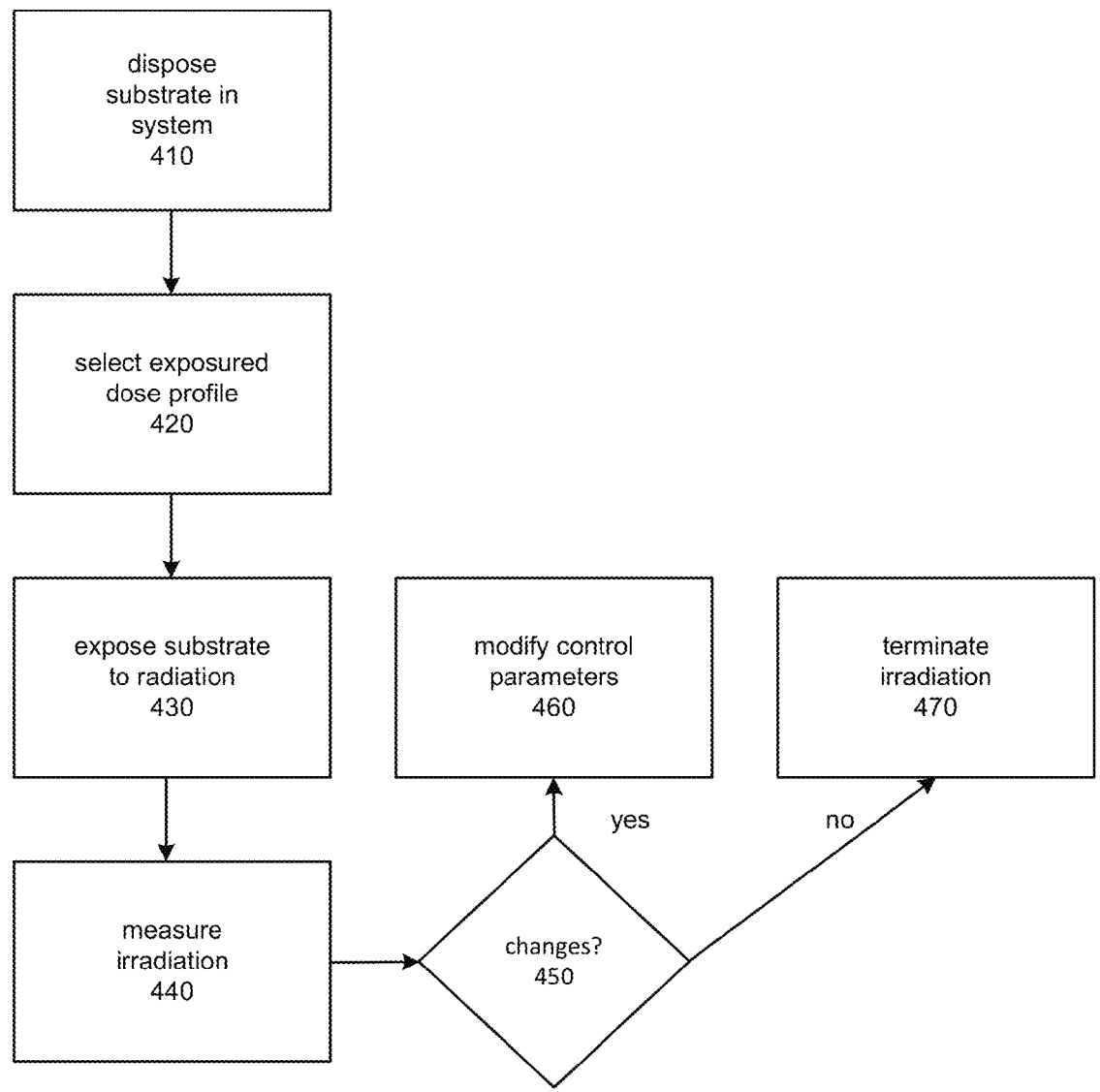
FIG. 4 is a substrate treatment method according to an embodiment of the invention.

FIG. 4 is a substrate treatment method 400 according to an embodiment of the invention. A substrate may be disposed on a substrate support 410 in a UV flood exposure treatment system. A UV flood exposure dose profile 420 may be selected. The substrate may be exposed to UV flood irradiation 430 from a UV source 300. According to the embodiments presented below, exposing the substrate to UV flood irradiation may comprise dose homogenization. In some embodiments, UV source 300 radiation may be measured 440, and the system 310 may determine if changes to the control settings are required to meet the profile (e.g., if UV source 300 performance has degraded) 450. If changes are needed, the control parameters may be modified 460. When the selected UV flood exposure dose profile is achieved, the UV flood irradiation may be terminated 470.

Dose Exposure Profiling

Achieving a selected dose profile, such as a homogenous profile, during UV flood irradiation exposure may be performed to improve a desired exposure for a substrate. A selected dose profile may be achieved by controlling at least one of a substrate rotation rate, a UV source scanning rate, a substrate scanning rate, a UV source power setting, a distance from the UV source to the substrate, a UV source aperture setting, an angle of incidence of UV flood irradiation on the substrate, and/or a UV source focus position to achieve the selected UV flood exposure dose profile. Homogenization circuit 320 or a dose profile selection circuit may determine settings, and processing control circuit 340 may use the settings to control substrate processing.

Figure 2:
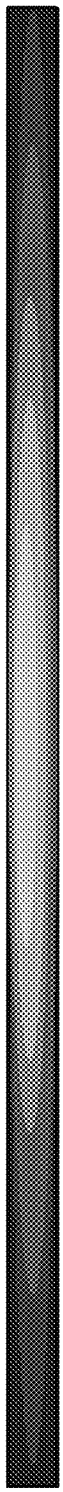
FIG. 2 is a sample UV intensity map.
Figure 5:
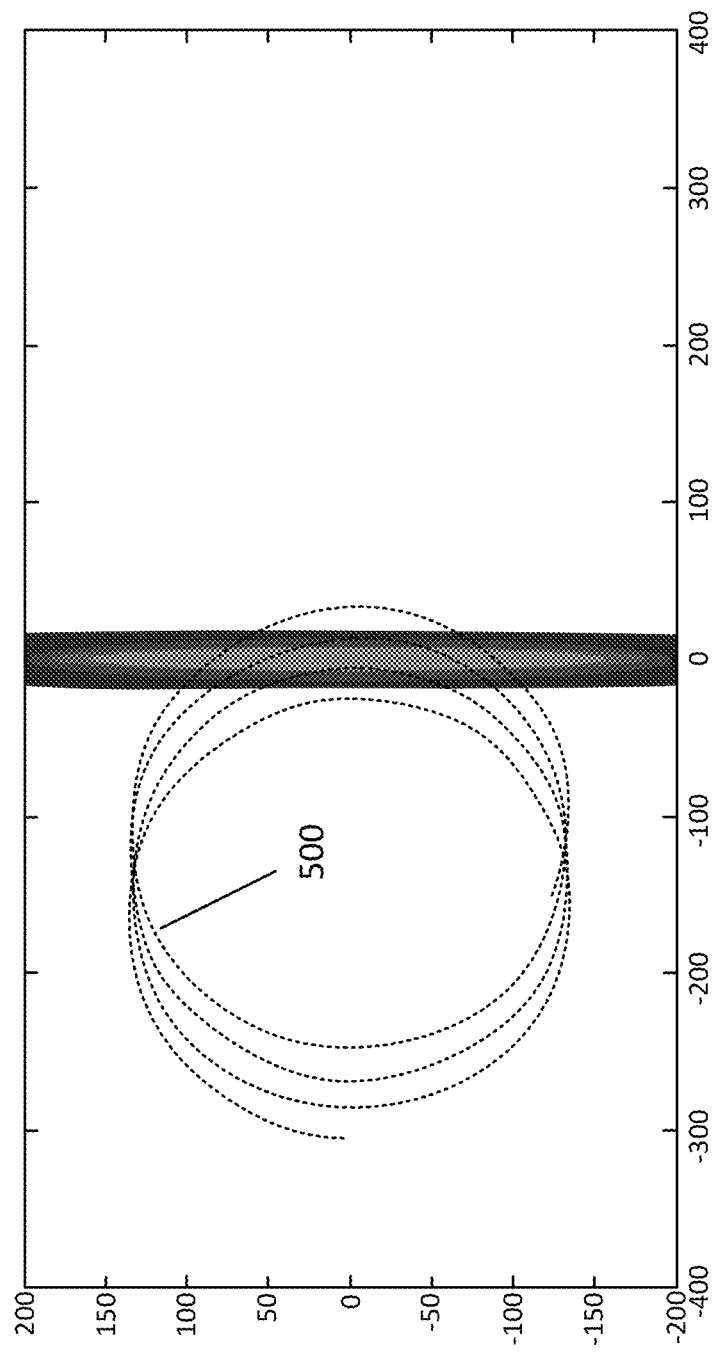
FIG. 5 is a path taken by a point on a wafer according to an embodiment of the invention.
Figure 6:
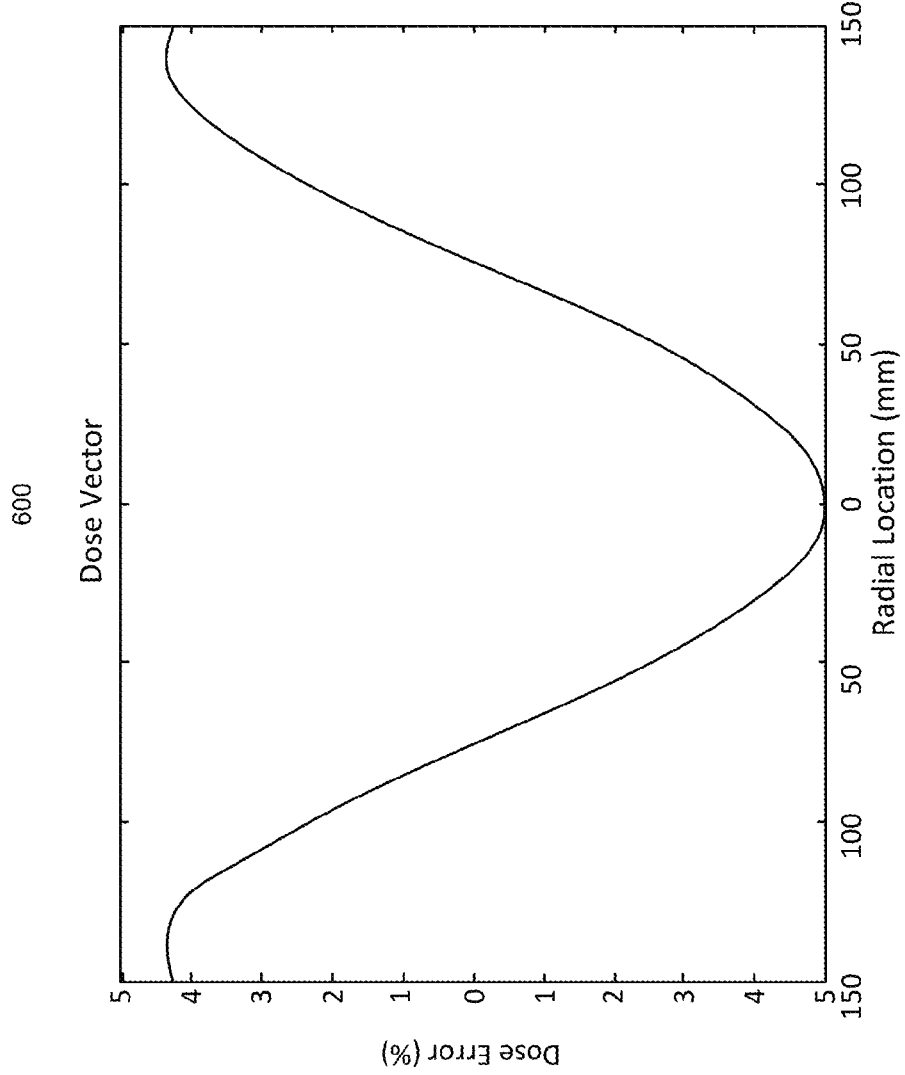
FIG. 6 is an uncorrected dose error vs. radius for a wafer according to an embodiment of the invention.

In some embodiments, a fixed rotation speed and fixed translation speed may be combined to homogenize a non-uniform slit constant dose exposure (e.g., created by a light bar without an aperture or a source that has a slit aperture between itself and the substrate) or otherwise achieve a selected profile. FIG. 5 is a path 500 taken by a point on a wafer according to an embodiment of the invention. As the wafer is rotated and translated under the UV source (located at point 0 on the horizontal scale), any given point on the wafer may be exposed to varying light intensity due to the inconsistent light intensity of the source. For example, when the point is rotated and translated to be directly under the center of the UV source, it may receive more intense light than when it is rotated and translated to be directly under an outer corner of the source. When rotation speed and translation speed are optimized, fixed speed rotation alone may partially normalize/average a non-uniform intensity slit to produce a radially dependent intensity signature that may be significantly uniform through rotation angle theta for any given radius. For fixed rotation speed alone without fixed translation speed, the lamp source may need to be a minimum length of the radius of the wafer and positioned such that one short axis of the light bar is at/near the origin of the rotating wafer to ensure complete exposure of the wafer. Adding fixed scan rate translation of a constant speed with a rotating wafer under a light slit may allow for some alteration of the radially dependent signature due to integrated time differences experienced by different parts of the rotating wafer under the source (e.g. center to edge). An example of a radially dependent signature following constant rotation and constant scan rate translation can be found in FIG. 6. FIG. 6 is a dose error vs. radius graph 600 for a wafer. A variable dose error percentage (approximately 9% variation in this example) may be exhibited based on radial location on the wafer, with 0 representing the center, and +/−150 representing the outer edges. With a centered light bar (e.g., center of light bar is over center origin of rotating wafer) and under fixed rotation and fixed translation speed conditions, the center of the wafer may experience exposure for only a short time under the lamp (as defined by slit width/scan rate). Under fixed (constant) rotation, fixed (constant) scan rate translation, and fixed (constant) power conditions, alteration of the radially dependent signature may be dependent on some or all of the following criteria:

1. source slit non-uniformity signature (e.g., as shown in FIG. 2)
2. physical relationship of the exposure slit to rotating wafer origin
3. exposure slit length and width
4. constants chosen for rotation rate/translation scan rate.

Figure 7:
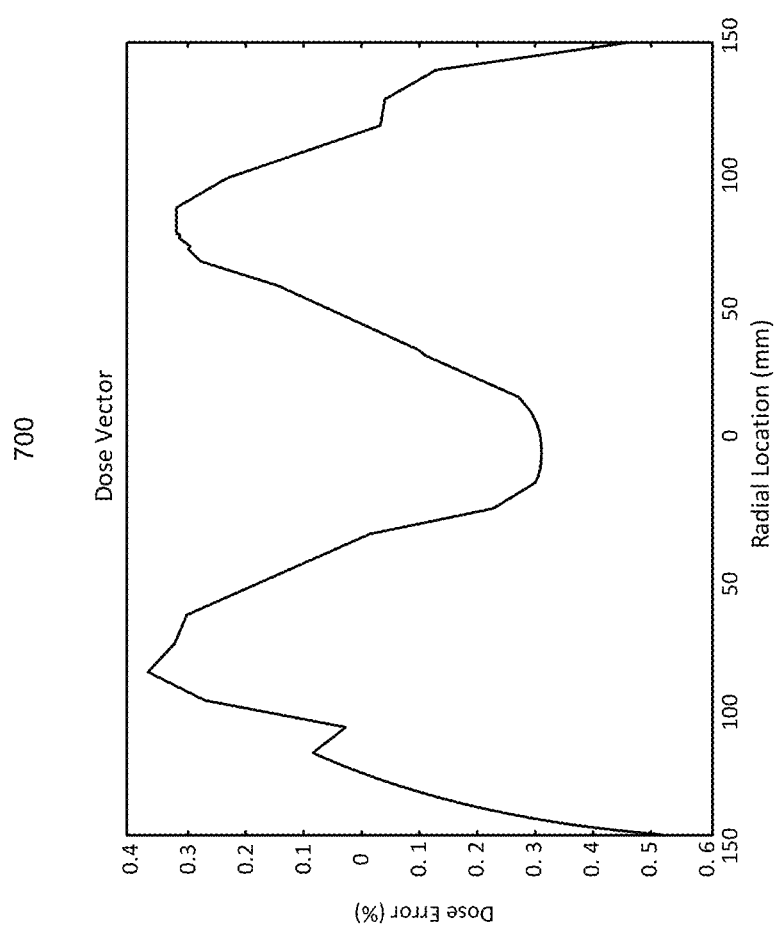
FIG. 7 is a corrected dose error vs. radius for a wafer according to an embodiment of the invention.

FIG. 7 is a dose error vs. radius graph 700 for a wafer according to an embodiment of the invention. By varying one or more dose homogenization settings, dose error variation may be reduced significantly (e.g., to approximately 0.9% variation in this example).

In some embodiments of the dose homogenization concept, a variable exposure dose may be provided through translation at constant scan rate and constant rotation speed to homogenize for intensity differences across the slit and integrated exposure time differences from rotation and translation. The default radial signature (e.g., with constant exposure dose, constant scan rate translation, and constant rotation rate as shown in FIG. 6) may be obtained. The inverse functional form may be approximately applied to source power through the translation (time) to further homogenize the signature (e.g., to improve the signature from that shown in FIG. 6 to the signature of FIG. 7 or better). The inverse functional form for this embodiment as well as subsequent embodiments may be obtained by normalizing the function of FIG. 6 and subtracting the normalized function from 1. Under fixed (constant) rotation, fixed (constant) scan rate translation, and variable source power conditions, alteration of the radially dependent signature may be dependent on some or all of the following criteria:

1. source slit non-uniformity signature (e.g., as shown in FIG. 2)

2. physical relationship of exposure slit to rotating wafer origin
3. exposure slit length and width
4. constants chosen for rotation rate/translation scan rate
5. functional form of variable power applied during translation.

In some embodiments of the dose homogenization concept, a variable scan rate may be provided through translation at constant power and constant rotation speed to homogenize for intensity differences across the slit as well as integrated exposure time differences from rotation and translation. The default radial signature (e.g., with constant exposure dose, constant scan rate translation, and constant rotation rate as shown in FIG. 6) may be obtained. The inverse functional form may be approximately applied to the scan rate (e.g., scan velocity) through translation (time) to further homogenize the signature (e.g., to improve the signature from that shown in FIG. 6 to the signature of FIG. 7 or better). Under fixed (constant) rotation, fixed (constant) power, and variable scan rate conditions, alteration of the radially dependent signature may be dependent on some or all of the following criteria:
1. source slit non-uniformity signature (e.g., as shown in FIG. 2)
2. physical relationship of exposure slit to rotating wafer origin
3. exposure slit length and width
4. constants chosen for rotation rate/power
5. functional form of variable scan rate applied during translation.

In some embodiments of the dose homogenization concept, a variable scan rate and variable power may be provided through translation with a constant rotation speed to homogenize for intensity differences across the slit and integrated exposure time differences from rotation and translation. The default radial signature (e.g., with constant exposure dose, constant scan rate translation, and constant rotation rate as shown in FIG. 6) may be obtained. An optimized co-dependent functional form may be applied to scan rate/power through translation (time) to further homogenize the signature (e.g., to improve the signature from that shown in FIG. 6 to the signature of FIG. 7 or better). Under fixed (constant) rotation, variable power, and variable scan rate conditions, alteration of the radially dependent signature may be dependent on some or all of the following criteria:
1. source slit non-uniformity signature (e.g., as shown in FIG. 2)
2. physical relationship of exposure slit to rotating wafer origin
3. exposure slit length and width
4. constants chosen for rotation rate
5. functional form of variable scan rate applied during translation
6. functional form of variable power applied during translation.

In some embodiments of the dose homogenization concept, a variable exposure dose may be provided through translation at constant power and constant rotation speed to homogenize for intensity differences across the slit and integrated exposure time differences from rotation and translation. The default radial signature (e.g., with constant exposure dose, constant scan rate translation, and constant rotation rate as shown in FIG. 6) may be obtained. The inverse functional form may be approximately applied to the width of the slit-shaped source aperture through translation (time) to further homogenize the signature (e.g., to improve the signature from that shown in FIG. 6 to the signature of FIG. 7 or better). The width of the slit-shaped source aperture may be controlled by a stepper motor, for example. Varying the width may control the amount of light transmitting the aperture and thereby control the time dependent exposure dose of the substrate. Under fixed (constant) rotation, fixed (constant) power, variable scan rate conditions, alteration of the radially dependent signature may be dependent on some or all of the following criteria:
1. source slit non-uniformity signature (e.g., as shown in FIG. 2)
2. physical relationship of exposure slit to rotating wafer origin
3. exposure slit length and width
4. constants chosen for rotation rate/power
5. functional form of variable aperture width applied during translation.

In some embodiments of the dose homogenization concept, a variable exposure dose may be provided through translation at constant power and constant rotation speed to homogenize for intensity differences across the slit, formed by a slit-shaped source aperture, as well as integrated exposure time differences from rotation and translation. The default radial signature (e.g., with constant exposure dose, constant scan rate translation, and constant rotation rate as shown in FIG. 6) may be obtained. The inverse functional form may be approximately applied to the relative height between the source and rotating/translating substrate through translation (time) to further homogenize the signature (e.g., to improve the signature from that shown in FIG. 6 to the signature of FIG. 7 or better). The relative height between the source and rotating/translating substrate may be controlled by a stepper motor, for example. Varying the height may control the amount of light transmitting through the aperture for light sources that diverge significantly with distance and thereby control the time dependent exposure dose of the substrate. The stepper motor may move the light source or the rotating/translating substrate. Under fixed (constant) rotation, fixed (constant) power, variable scan rate conditions, alteration of the radially dependent signature may be dependent on some or all of the following criteria:
1. source slit non-uniformity signature (e.g., as shown in FIG. 2)
2. physical relationship of exposure slit to rotating wafer origin
3. exposure slit length and width
4. constants chosen for rotation rate/power
5. functional form of variable height applied during translation.

In some embodiments of the dose homogenization concept, a variable exposure condition may be provided through translation at constant power and constant rotation speed to homogenize for intensity differences across the slit as well as integrated exposure time differences from rotation and translation. To accomplish the variable exposure condition, optical elements (e.g., mirror or lens) may be placed between source and substrate. Such embodiments may be used in combination with the other embodiments described above or independently. An oscillating mirror may be used to vary the light signature relative position along the central scanning axis. Other optical elements (e.g., lenses) may be used to vary the signature itself (e.g., the size, shape, and/or profile) during rotation and translation. In the oscillating mirror variant for changing the light signature relative position along the central scanning axis, intentional high frequency jitter may be introduced into the light placement relative to the central axis of translation during rotation and translation to introduce some averaging of local non-uniformities with the light source. In the lens variant for the manipulation of the signature during rotation and translation, the default radial signature (e.g., with constant exposure dose, constant scan rate translation, and constant rotation rate as shown in FIG. 6) may be obtained, and the inverse functional form may be approximately applied to the relative height or angle of optical element to that of the source through translation (time) to further homogenize the signature (e.g., to improve the signature from that shown in FIG. 6 to the signature of FIG. 7 or better). The relative height or angle of the optical element to the source may be controlled by a stepper motor, for example. Varying the height or angle of optical element may control the amount of light transmitting through the aperture (e.g., by changing focal point) and thereby control the time dependent exposure dose of the substrate. Under fixed (constant) rotation, fixed (constant) power, variable scan rate conditions, alteration of the radially dependent signature may be dependent on some or all of the following criteria:

1. source slit non-uniformity signature (e.g., as shown in FIG. 2)
2. physical relationship of exposure slit to rotating wafer origin
3. exposure slit length and width
4. constants chosen for rotation rate/power
5. functional form of variable height or angle of optical element applied during translation.

The descriptions of the embodiments presented above have assumed a goal of cross-wafer minimization of differences in integrated energy, but the same methods may be used to improve initial non-uniformity and intentionally induce a radial integrated dose systematic variable signature to account for external process non-uniformities (e.g., wafer to edge etch bias).

Also, while a non-uniform slit (e.g., created by a light bar without an aperture or a source that has a slit aperture between itself and substrate) is used with the embodiments mentioned above, the embodiments may be applied to systems having any shape of illumination for improved cross-substrate integrated dose uniformity.

Simulation

Figure 8:
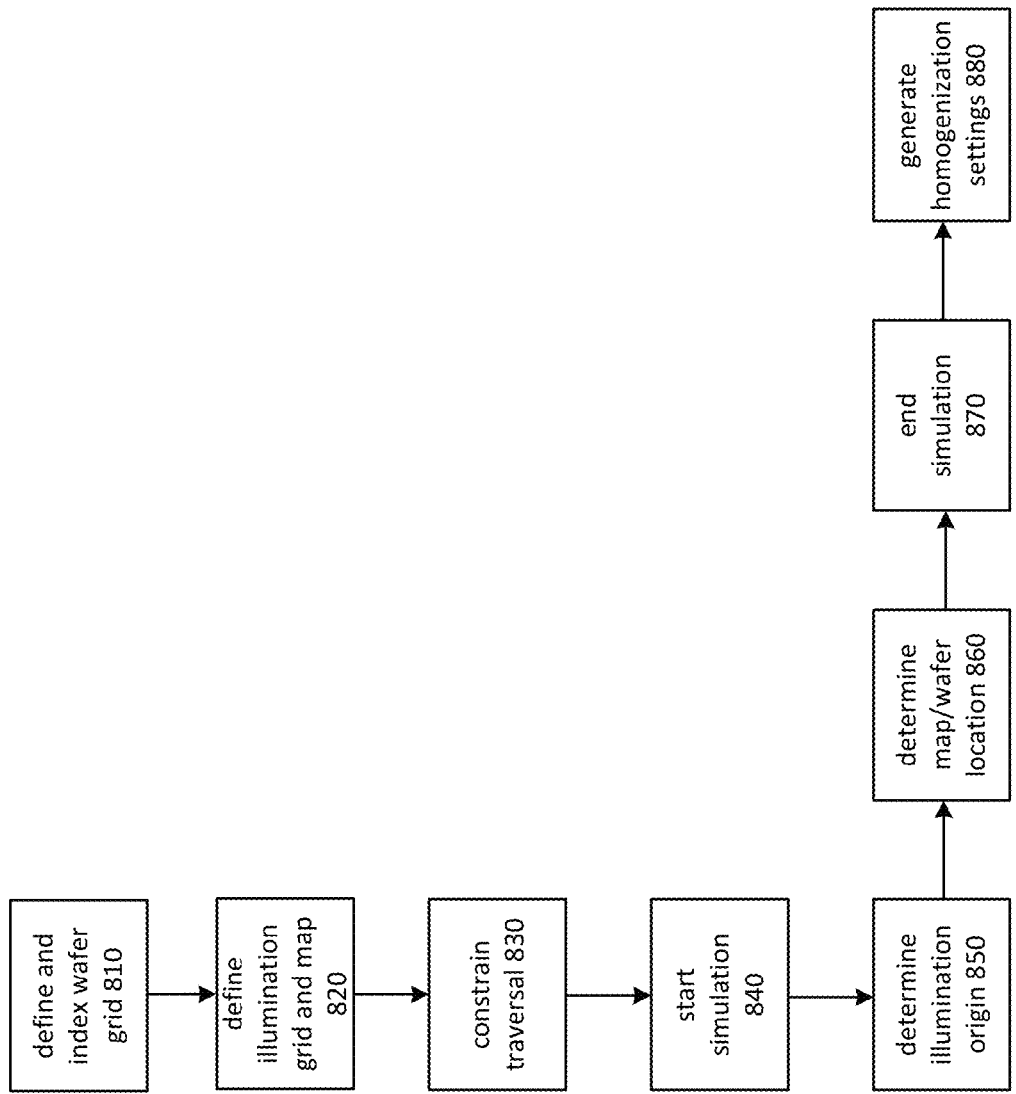
FIG. 8 is a dose homogenization simulation method according to an embodiment of the invention.

FIG. 8 is a dose homogenization simulation method 800 according to an embodiment of the invention. Homogenization circuit 320 may be configured to perform homogenization simulation in some embodiments. This method 800 may be used to determine settings for dose homogenization during UV exposure, for example based on controlling at least one of a substrate rotation rate, a UV source scanning rate, a substrate scanning rate, a UV source power setting, a distance from the UV source to the substrate, a UV source aperture setting, an angle of incidence of UV flood irradiation on the substrate, and/or a UV source focus position to achieve the selected UV flood exposure dose profile as described above.

Figure 9:
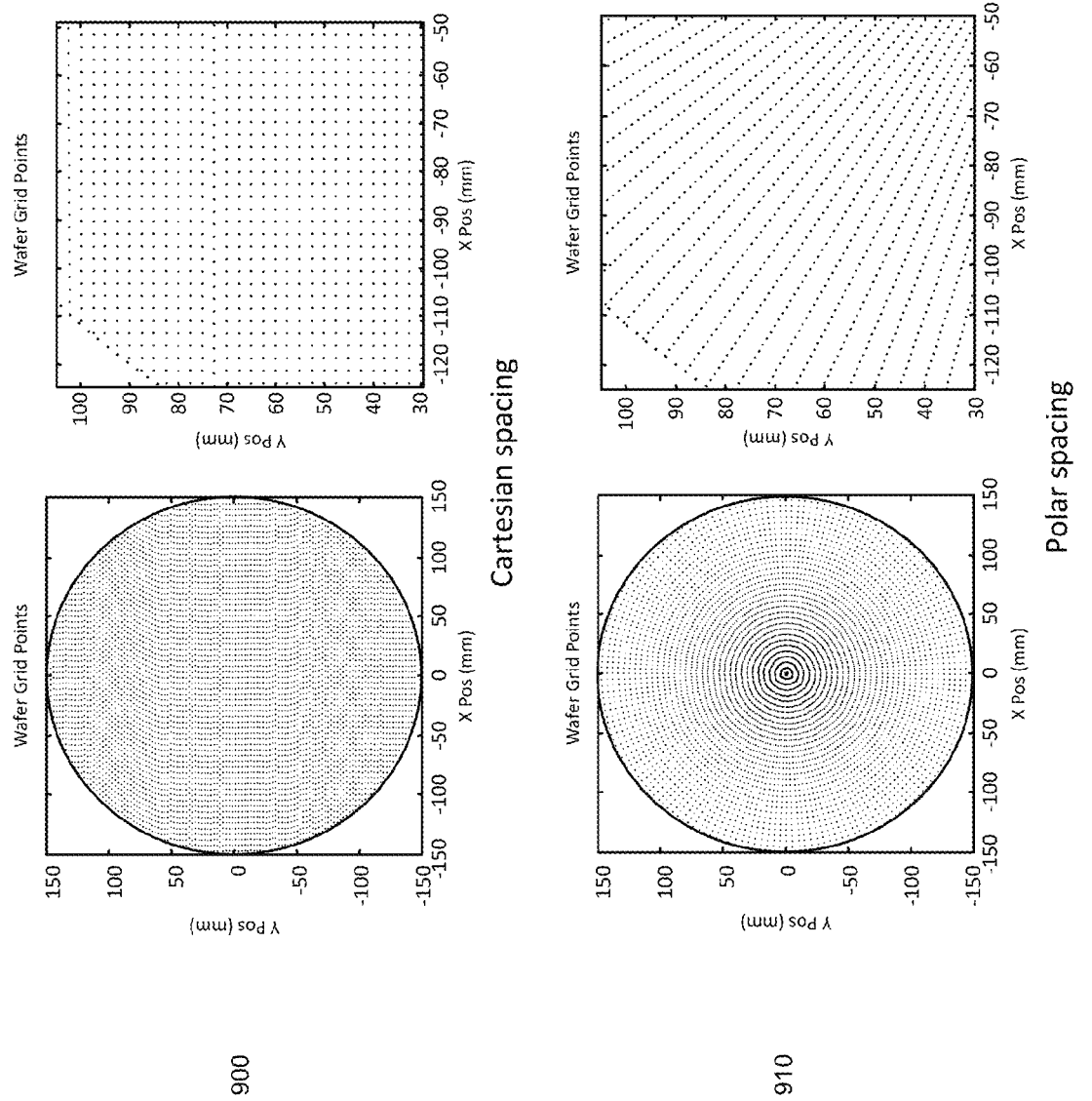
FIG. 9 is a wafer grid according to an embodiment of the invention.

A wafer grid may be defined 810 for a substrate to be processed. As shown in FIG. 9, the wafer grid may be based on Cartesian spacing 900 or polar spacing 910. Grid points may be indexed, and an (r, θ) location of each indexed point may be determined.

Figure 10:
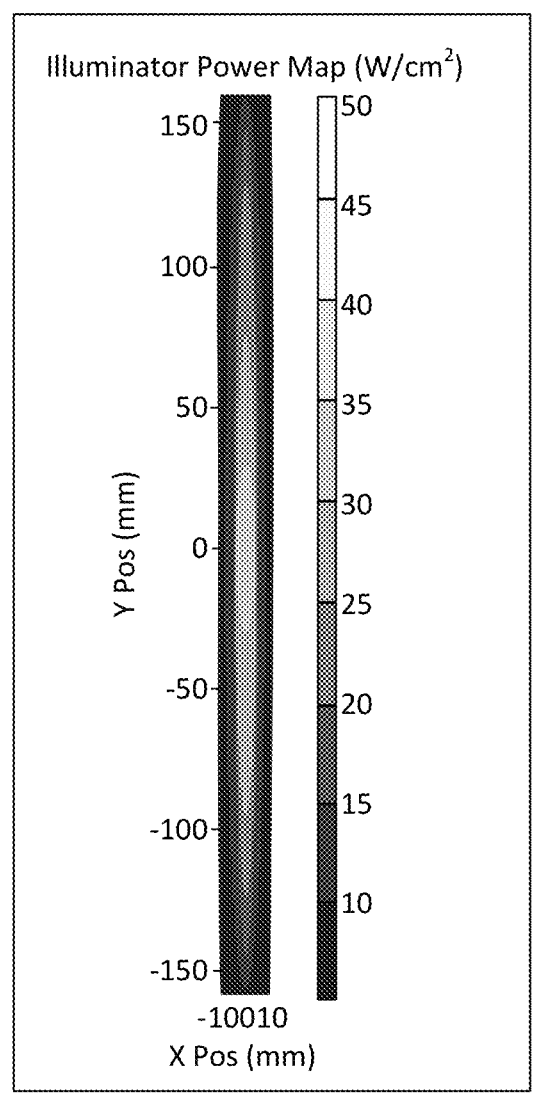
FIG. 10 is an illumination map according to an embodiment of the invention.

An illumination grid and map may be defined 820. FIG. 10 shows an example illumination map 1000. An illumination shape may be defined either by defining options (e.g., specifying known characteristics of a UV source) or by inputting a custom map (e.g., via a text file). A uniform rectangular grid matrix may be assigned to the illumination map, and the power for each grid point may be interpolated. This grid may be at a higher spatial resolution than the wafer grid. The center of the illumination map may be defined as the illumination origin.

Figure 11:
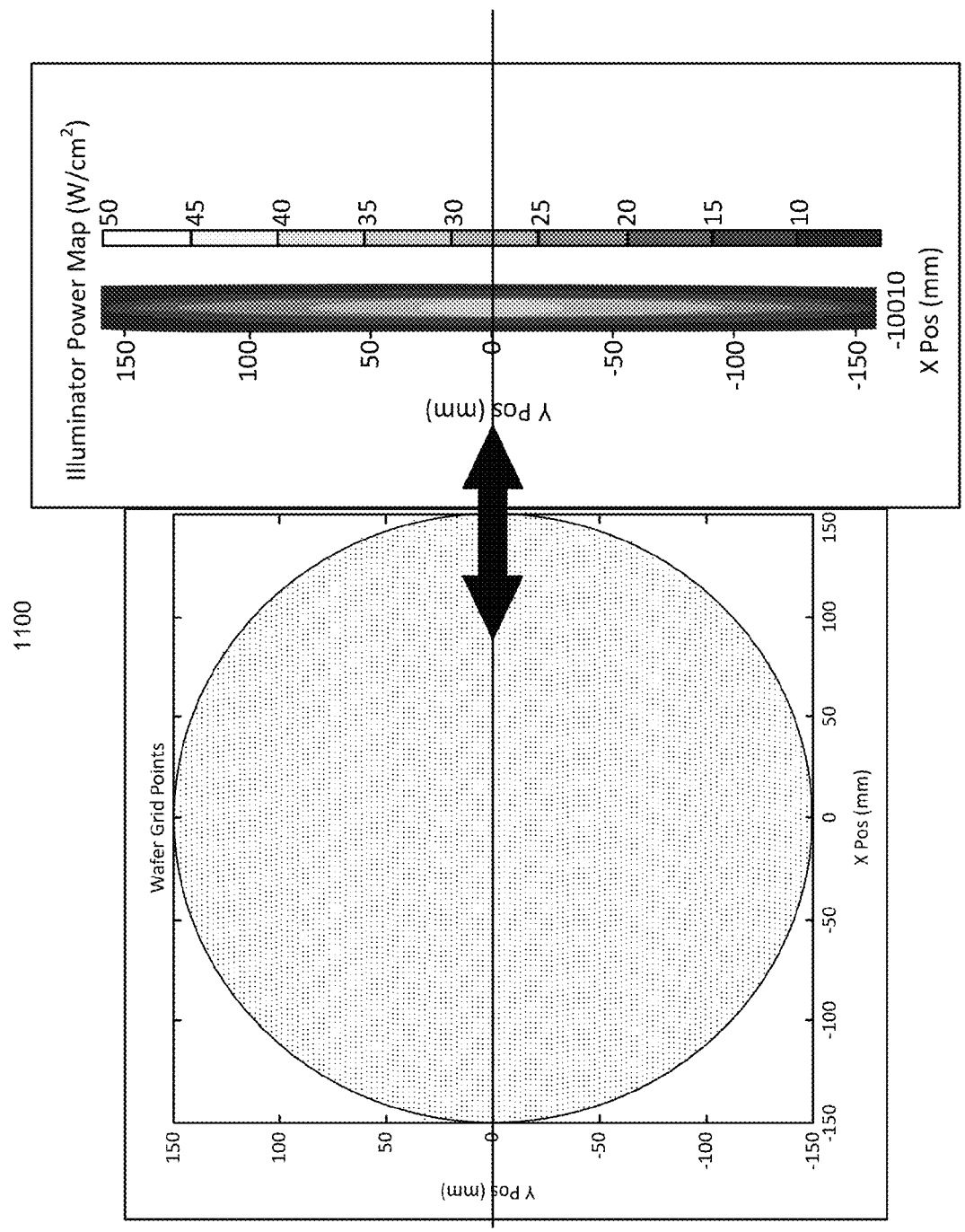
FIG. 11 is a traversal map according to an embodiment of the invention.

Assumptions about wafer traversal of the source may be made 830. For example, as shown in the map 1100 of FIG. 11, the illumination origin may be assumed to be traversing along the central axis of the wafer plane and may be assumed to pass through the wafer plane origin. Under this assumption, there may be no mathematical difference whether the wafer or the illumination source is moving with respect to the other.

A simulation using the defined wafer grid, illumination grid and map, and traversal may be performed 840, in which the wafer is traversed along the source. An example simulation process is described in greater detail with respect to FIG. 12 below. At each simulation iteration (e.g., each simulator time step), a location of the illumination origin within the wafer coordinate system may be determined 850 by $R_n = R_{n-1} + \Delta R$ (where $\Delta R$ is delta change in radius and is determined based on scan rate*simulation time step) and $\theta_n = \theta_{n-1} + \Delta\theta$ (where $\Delta\theta$, delta change in theta and is determined based on RPM*simulation time step). $R_n, \theta_n$ may represent the wafer location that is directly under the illumination origin at the time step.

Additionally, it may be determined whether the illumination map is over a wafer indexed location 860. First, if a pacman aperture is defined, then all wafer indexed grid θ points outside of $\theta_n - pacman_{angle}/2 \sim \theta_n + pacman_{angle}/2$ may be excluded. Next, based on $R_n, \theta_n$, the relative distance of all remaining wafer indexed grid points may be determined. If a wafer indexed grid point is found to be under the illumination (for the current simulation step), then the power at that point may be determined. This may be done by finding the relative distance between $R_n, \theta_n$ and wafer grid point and then referencing the illumination power grid for the power that this wafer grid point is experiencing for the simulation step. For example, Wafer Pos(x,y)$_{Power(n)}$=Wafer Pos(x,y)$_{Power(n-1)}$+illumination time step*Illumination Power Map(relX, relY). If a wafer indexed grid point is not under the illumination, Wafer Pos(x,y)$_{Power(n)}$=Wafer Pos(x, y)$_{Power(n-1)}$.

The simulation may end 870 after all iterations are complete. A final map of Wafer Pos(x,y)$_{Power(n)}$ may be plotted, and statistics may be determined. Based on this, homogenization settings may be determined 880. For example, according to the embodiments described above, at least one of a substrate rotation rate, a UV source scanning rate, a substrate scanning rate, a UV source power setting, a distance from the UV source to the substrate, a UV source aperture setting, an angle of incidence of UV flood irradiation on the substrate, and a UV source focus position may be selected to homogenize dosing for the simulated system.

Figure 12:
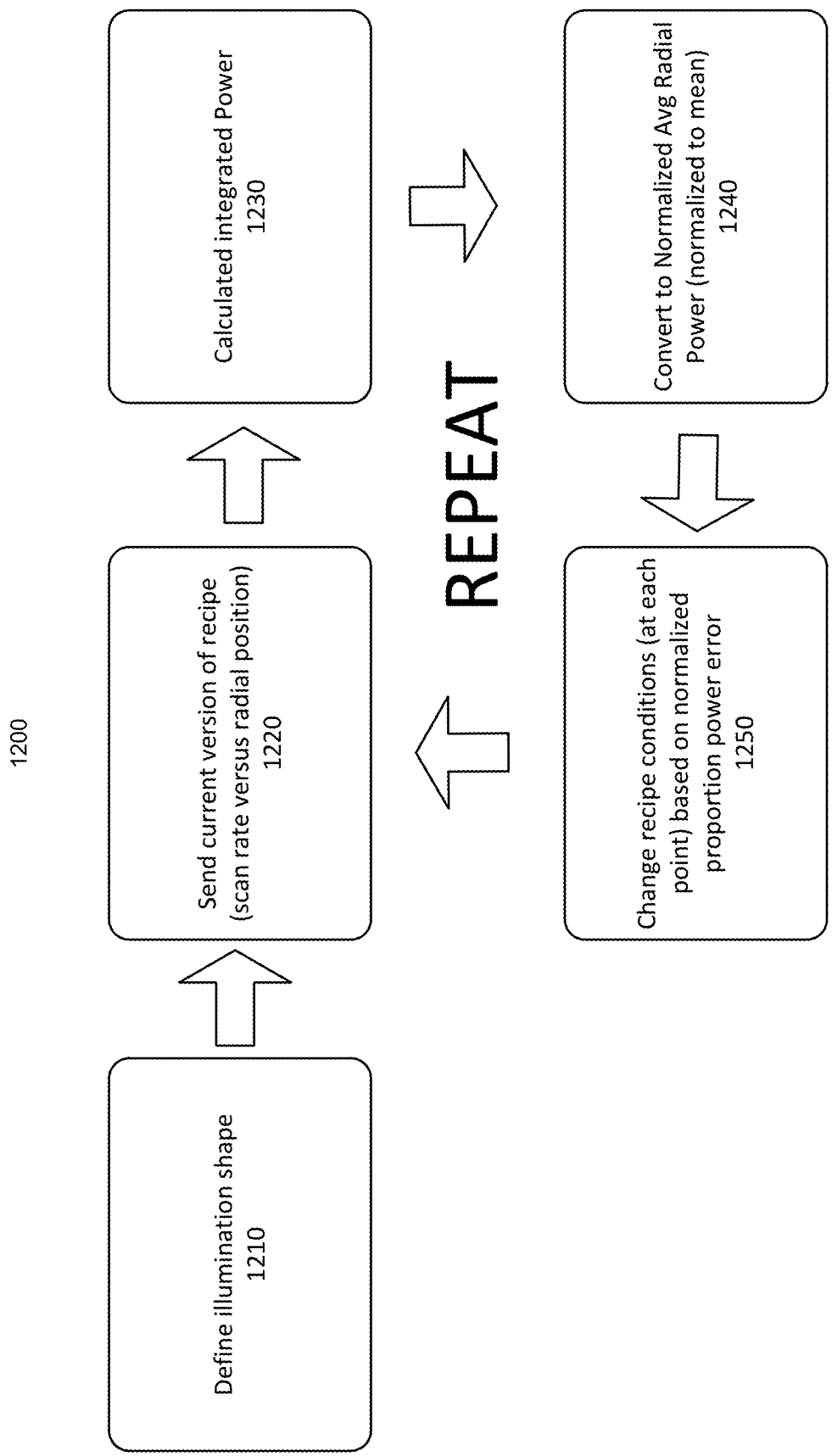
FIG. 12 is a dose homogenization simulation method according to an embodiment of the invention.
Figure 13:
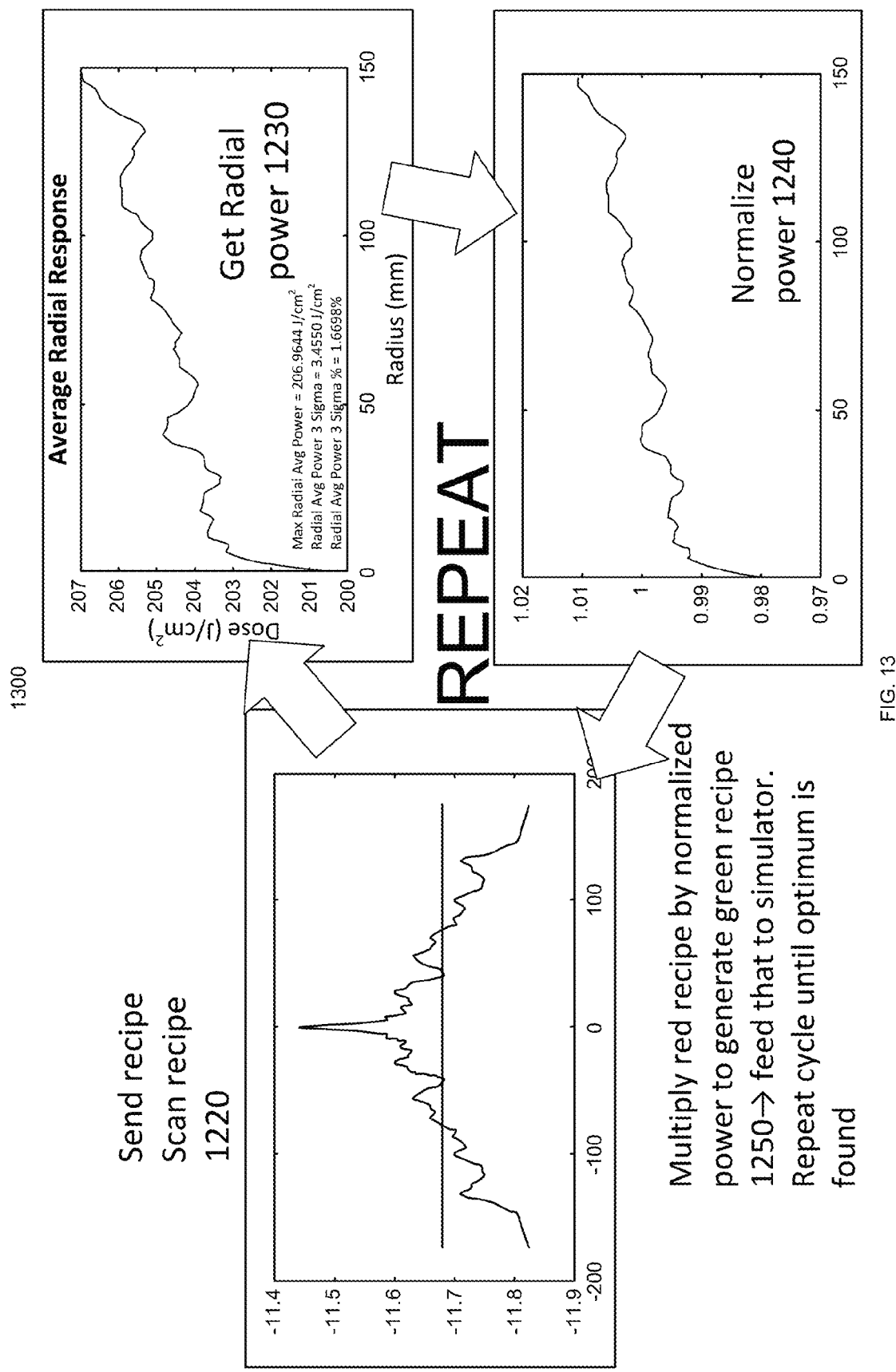
FIG. 13 is a dose homogenization simulation according to an embodiment of the invention.

FIG. 12 is a dose homogenization simulation method 1200 according to an embodiment of the invention. FIG. 13 is an example dose homogenization simulation 1300 according to an embodiment of the invention. The illumination shape may be defined 1210 (e.g., from the illumination grid and map generated above). A current version of a processing recipe (scan rate vs. radial position) may be loaded 1220. Integrated power for the recipe may be calculated 1230 and converted to normalized average radial power 1240 (e.g., normalized to the mean). Recipe conditions (e.g., scan rate and/or radial position) may be changed at each point based on normalized proportion power error 1250 and used as the next version of the processing recipe, for which steps 1220-1240 may be repeated. Steps 1220-1250 may be repeated multiple times (e.g., 3-8 iterations) until error is reduced to a satisfactory level.

Sensor Feedback

Figure 14:
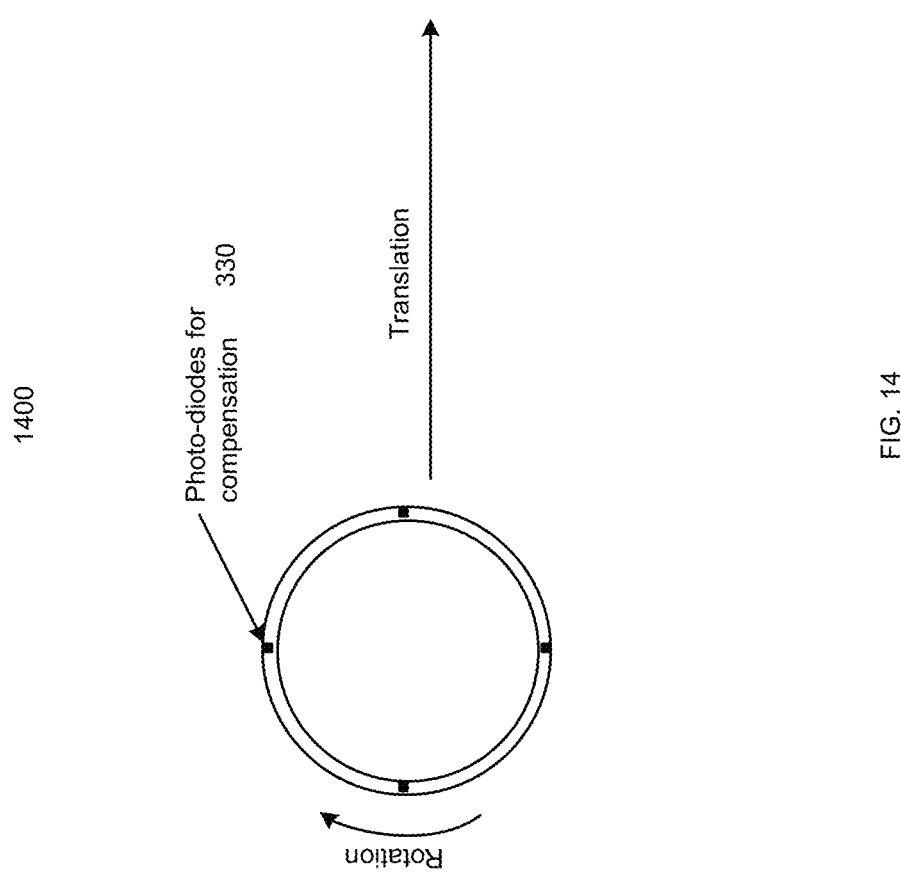
FIGS. 14-16 are sensor arrays according to embodiments of the invention.

The following sensor system and process control schemes may be used to control dose homogenization, for example according to one or more of the embodiments described above. In one example sensor system and process control scheme, wafer edge mounted photo-sensors 330 may be used to obtain real time slit non-uniformity information. For example, 3 or more UV photo-sensors 330 (e.g., 3 or more for redundancy to sensor failure and/or sensor mis-calibration) may be mounted on the rotating stage just outside the rotating wafer's edge (e.g., for a 300 mm wafer, mounted at radius 152 mm), as shown in sensor array 1400 of FIG. 14. The UV photo-sensors 330 may be equally spaced along the arc of the mounting annulus (e.g., 3 sensors mounted at 120 degree intervals). During rotation/translation, each sensor 330 may sample a large portion of the light bar area, because each sensor 330 may see multiple areas of the light bar through time (see FIG. 5, for example). Sensed information may be used to understand the current average power of the lamp as well as the current light bar non-uniformity signature. Homogenization circuit 320 may receive sensed information and use it to determine settings, and processing control circuit 340 may use the settings to control substrate processing. Both current average power and current non-uniformity signature may be used in a process control scheme to feedback settings to a next wafer or lot, for example to modify one or more of the following:
1. a power setting offset/calibration
2. functional form of variable scan rate applied during translation
3. functional form of variable power applied during translation
4. a functional form of variable source aperture width applied during translation.

Figure 15:
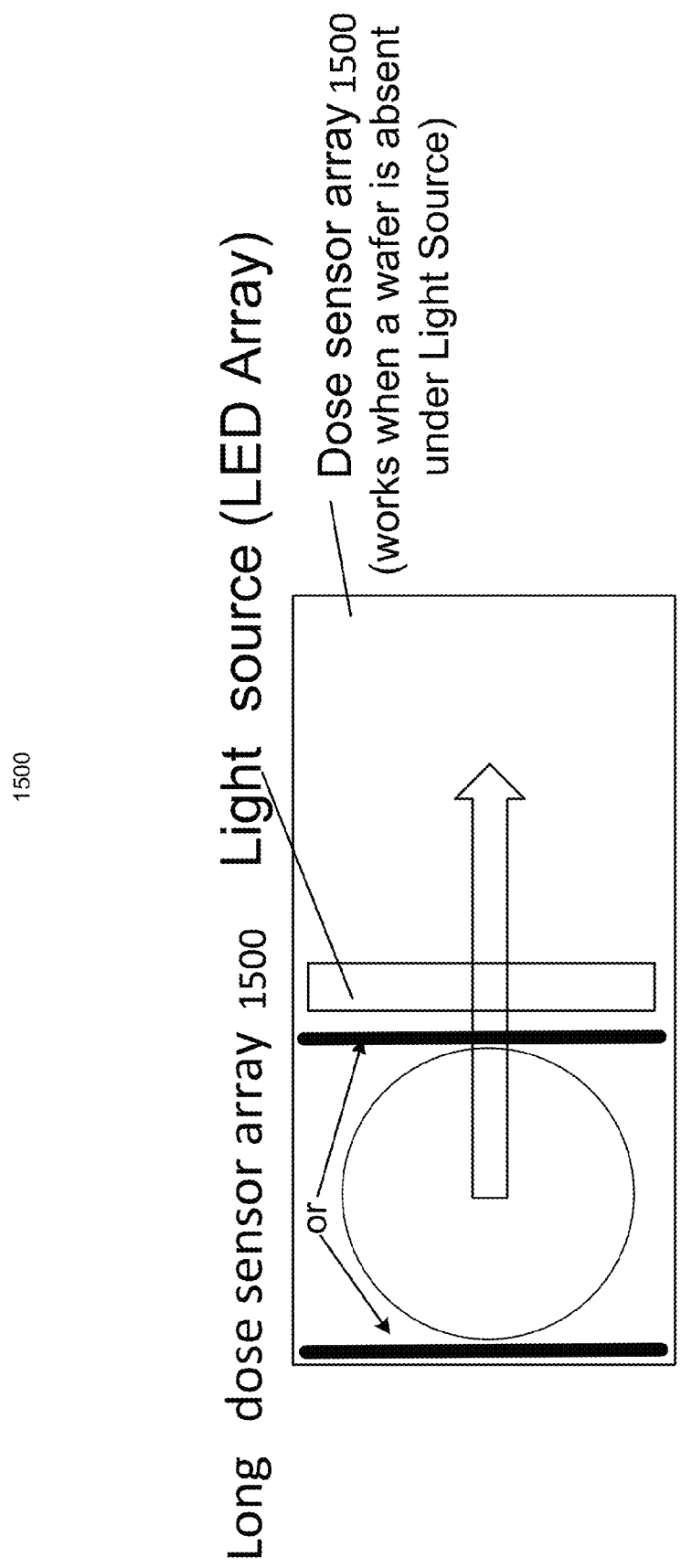

In another example sensor system and process control scheme, a bar/slit CCD array 330 of length equal to or greater than the rotating wafer diameter may be mounted on the translation stage either in front of or behind the rotating stage (e.g., so as not to be under the rotating stage/wafer, but still obtain scanned data under the light bar with each translation), as shown in sensor array 1500 of FIG. 15. The scanned data may be used to understand the current average power of the lamp as well as the current light bar non-uniformity signature. Homogenization circuit 320 may receive sensed information and use it to determine settings, and processing control circuit 340 may use the settings to control substrate processing. Both current average power and current non-uniformity signature may be used in a process control scheme to feedback settings to a next wafer or lot, for example to modify one or more of the following:
1. a power setting offset/calibration
2. functional form of variable scan rate applied during translation.

Figure 16:
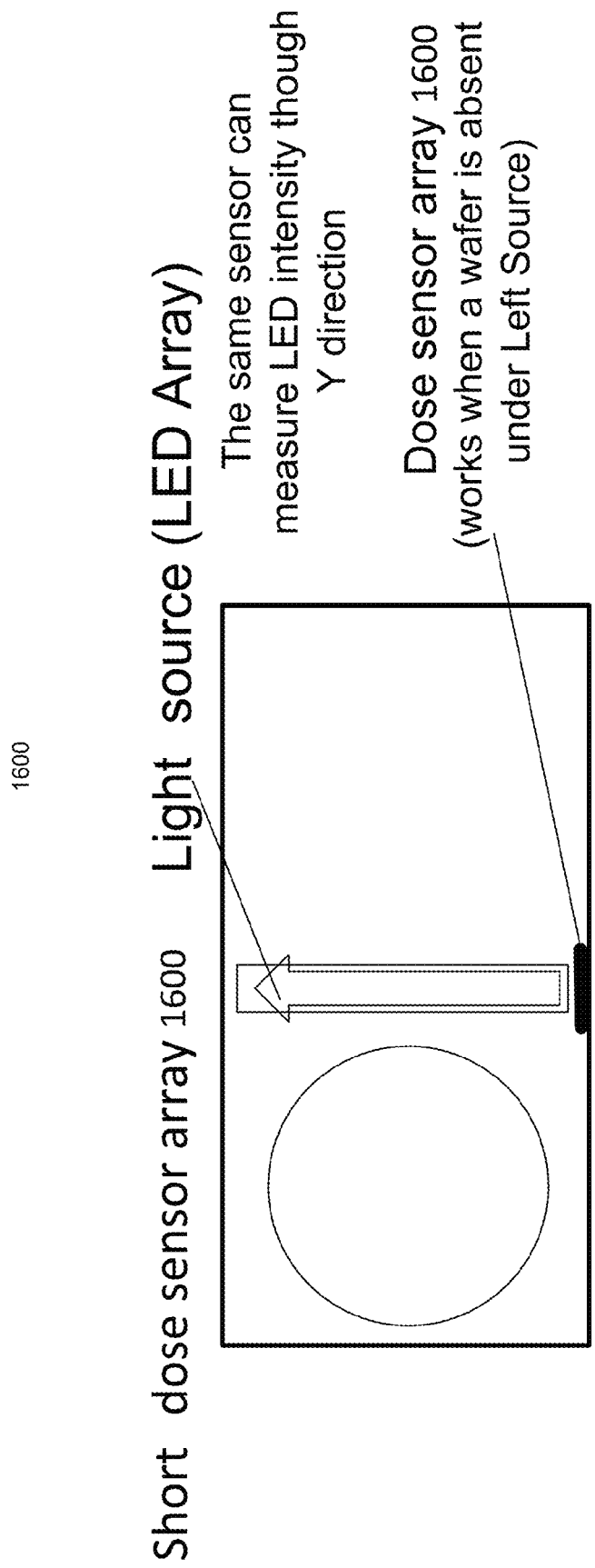

In another example sensor system and process control scheme, a motorized scanning bar/slit CCD array 330 of length equal to or greater than the illumination spread along the scanning/stage translating axis may be mounted perpendicular to the translation stage (e.g., so as not to strike the rotating/translating stage during non-use), as shown in sensor array 1600 of FIG. 16. During a time in which the substrate translation stage is not under the light source, the motorized scanning bar/slit CCD array 330 may scan under the light source and collect data. The collected data may be used to understand the current average power of the lamp as well as the current light bar non-uniformity signature. Homogenization circuit 320 may receive sensed information and use it to determine settings, and processing control circuit 340 may use the settings to control substrate processing. Both current average power and current non-uniformity signature may be used in a process control scheme to feedback settings to a next wafer or lot, for example to modify one or more of the following:
1. a power setting offset/calibration
2. functional form of variable scan rate applied during translation.

EXAMPLE

Figure 17:
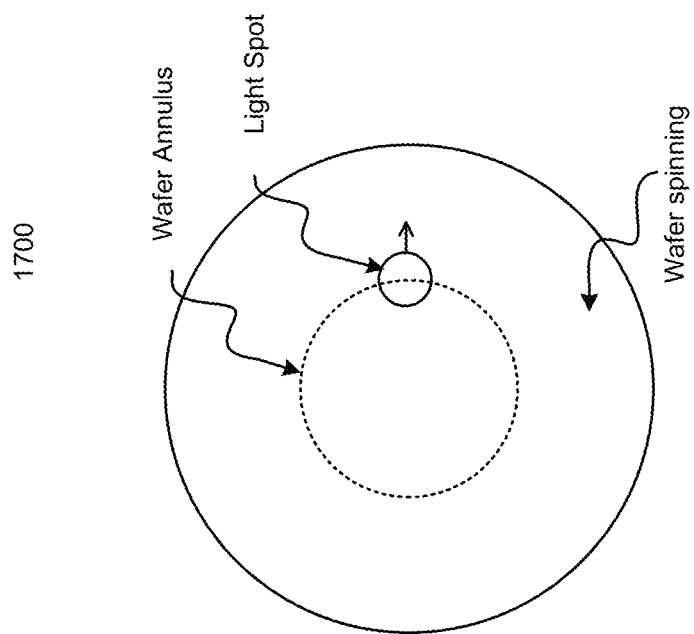
FIG. 17 is a wafer according to an embodiment of the invention.

In the following example, the dose homogenization above may be applied to the example wafer 1700 of FIG. 17. The wafer 1700 may spin counterclockwise, and a wafer annulus of interest may be located at a specific radius away from the center of the wafer 1700. If wafer 1700 is spinning much faster than the light spot scan velocity (or wafer scan velocity if light spot is at fixed position along central axis of scanning wafer), then we may assume the wafer annulus will pass under all areas of the light spot. The dwell time for any single rotation of the wafer 1700 may be the distance across the light spot divided by the angular velocity. The dwell time for all the rotations of the annulus under the light spot, after integrating, may be the area of the light spot divided by the product of circumference and light spot velocity (or wafer scan velocity if light spot is at fixed position along central axis of scanning wafer), as follows (where r is light spot radius and R is wafer radius):

$$t_{dwell} = \frac{(\pi r_{ls}^2)}{(2\pi R_{wafer})V_{ls}}$$

The dwell time for any radius may be a function of the light spot velocity (or wafer scan velocity if light spot is at fixed position along central axis of scanning wafer), which may be rearranged to give the light spot velocity as a function of dwell time, as follows:

$$V_{ls} = \frac{r_{ls}^2}{2R_{wafer}t_{dwell}}$$

To get the process time for the light spot to scan, the inverse light spot velocity formula may be integrated as follows:

$$t_{scan} = \int_{R_{start}}^{R_{end}} \frac{1}{V_{ls}} dR$$

However, the light spot velocity may go to infinity at the center, so calculation may begin at some fixed distance from the center. Accordingly, a definite integral may be obtained from the start radius to the end radius as follows:

$$t_{TOTAL} = \int_{R_{start}}^{R_{end}} \frac{1}{V_{ls}} dR + \frac{R_{start}}{V_{center}}$$

Finally, to get the total process time, the time it takes the light spot to move from the center to the start position may be added as follows:

$$t_{TOTAL} = \frac{t_{dwell}(R_{end}^2 - R_{start}^2)}{r_{ls}^2} + \frac{R_{start}}{V_{center}}$$

Equations 1800 for the calculations for a circular light spot shape may thus be as shown in FIG. 18. The equations 1800 may be used to achieve a goal, for example to find a scan recipe to fit within 60 seconds, given a light spot radius of 8 mm. This may proceed as follows:
1. Decide start position away from center, speed, and stop position:

$R_{start}$=0-20 mm@10 mm/s $R_{end}$=147 mm

2. Calculate dwell time for light spot scan:

$T_{dwell}$=(60−20/10)*8²/(147²−20²)

$T_{dwell}$=0.175 [sec]

3. Create Light Spot Formula:

$V_{ls}$=8²/(2*R*0.175)

$V_{ls}$=182.836/R [mm/s]

4. Check formula result:

$$t_{TOTAL} = \int_{20}^{147} \frac{R}{182.836} dR + \frac{20}{10}$$

$$t_{TOTAL} = \frac{(147^2 - 20^2)}{2 \times 182.836} + \frac{20}{10} = 60.000$$

Figure 19:
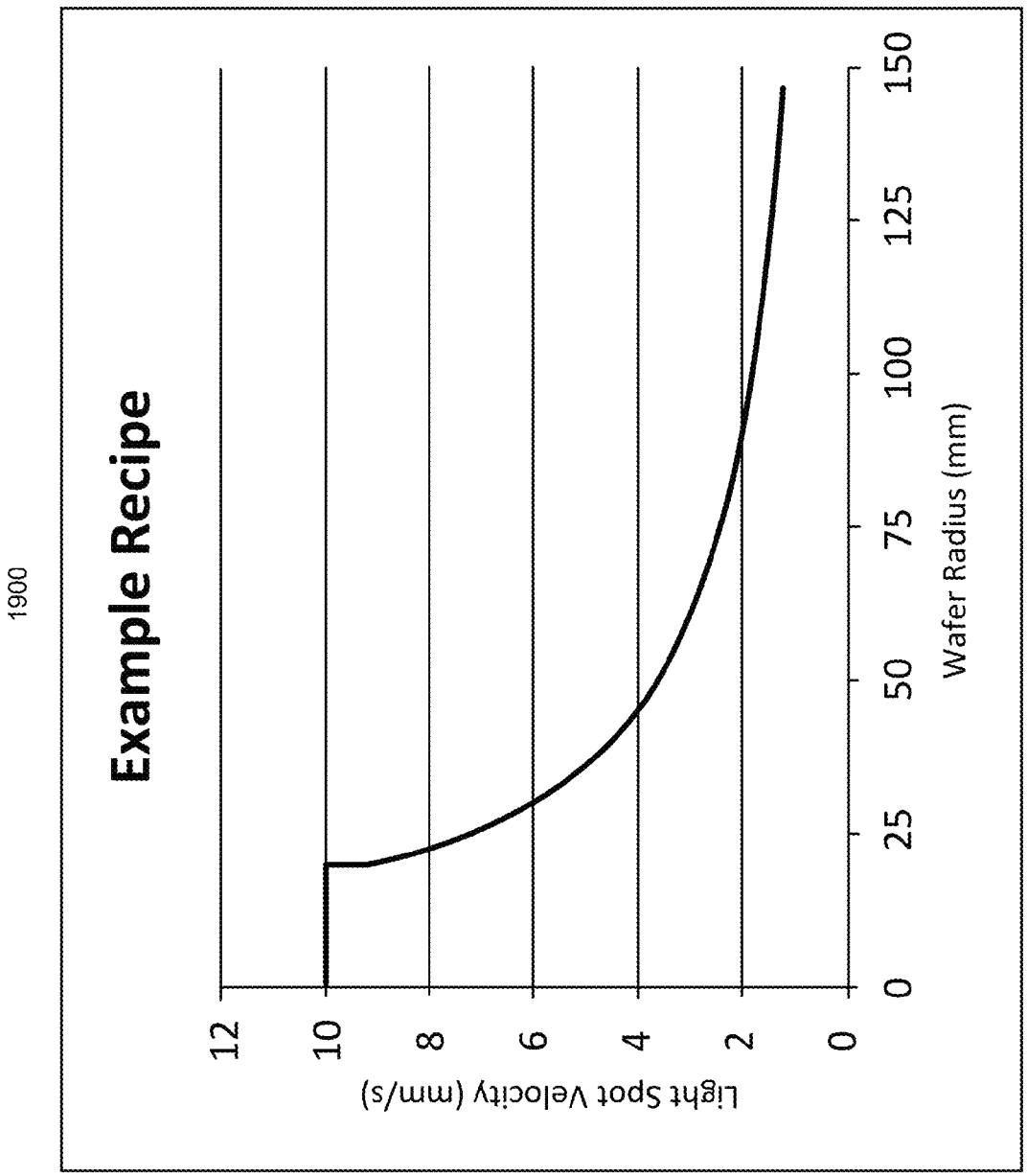
FIG. 19 is a processing recipe according to an embodiment of the invention

This may yield the example recipe 1900 shown in FIG. 19.

As discussed above, systems and methods relating to dose homogenization of a flood exposure process may combine rotation and translation to homogenize a non-uniform slit (or spot) exposure. Variable power at constant scan rate thru translation may be used to homogenize for intensity differences across slit (or spot) as well as exposure time differences from rotation and translation method—leading to a homogenized integrated power across wafer. Variable scan rate at constant power thru translation may be used to homogenize for intensity differences across slit (or spot) as well as exposure time differences from rotation and translation method—leading to a homogenized integrated power across wafer. Variable scan rate and variable power thru translation may be used to homogenize for intensity differences across slit (or spot) as well as exposure time differences from rotation and translation method—leading to a homogenized integrated power across wafer. Variable source aperture at constant scan rate thru translation may be used to homogenize for intensity differences across slit (or spot) as well as exposure time differences from rotation and translation method—leading to a homogenized integrated power across wafer. Variable relative height between source and substrate at constant scan rate thru translation may be used to homogenize for intensity differences across slit (or spot) as well as exposure time differences from rotation and translation method—leading to a homogenized integrated power across wafer. Variable relative height or angle between source and lens at constant scan rate thru translation may be used to homogenize for intensity differences across slit (or spot) as well as exposure time differences from rotation and translation method—leading to a homogenized integrated power across wafer. Oscillation of light signature relative position along central scanning axis during rotation and translation may be used to help average intensity differences across slit (or spot)—leading to a homogenized integrated power across wafer.

Additionally, wafer edge mounted rotating photo-sensors or translating CCD arrays may be used to get real time slit (or spot) non-uniformity information as well as average power information for use in APC control loops. A DC shift in power target may be applied for a next wafer (or next lot) due to observed average drift. A variable scan rate or variable dose thru translation change may be applied for a next wafer (or next lot) due to observed slit non-uniformity changes.

While various embodiments have been described above, it should be understood that they have been presented by way of example and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments.

In addition, it should be understood that any figures that highlight the functionality and advantages are presented for example purposes only. The disclosed methodology and system are each sufficiently flexible and configurable such that they may be utilized in ways other than that shown.

Although the term "at least one" may often be used in the specification, claims and drawings, the terms "a", "an", "the", "said", etc. also signify "at least one" or "the at least one" in the specification, claims and drawings.

Finally, it is the applicant's intent that only claims that include the express language "means for" or "step for" be interpreted under 35 U.S.C. 112(f). Claims that do not expressly include the phrase "means for" or "step for" are not to be interpreted under 35 U.S.C. 112(f).

What is claimed is:

1. A method of treating a substrate, comprising:
    disposing the substrate on a substrate support in a flood exposure treatment system;
    selecting a flood exposure dose profile; and
    exposing the substrate to flood irradiation from a source, terminating the flood irradiation when the selected flood exposure dose profile is achieved,
    wherein exposing the substrate to flood irradiation comprises controlling at least one of a substrate rotation rate, a source scanning rate, a substrate scanning rate, a source power setting, a distance from the source to the substrate, a source aperture setting, an angle of incidence of flood irradiation on the substrate, and a source focus position to achieve the selected flood exposure dose profile.

2. The method of claim 1, wherein exposing the substrate to flood irradiation comprises controlling at least two parameters selected from a group consisting of the substrate rotation rate, the source scanning rate, the substrate scanning rate, the source power setting, the distance from the source to the substrate, the source aperture setting, the angle of incidence of flood irradiation on the substrate, and the source focus position.

3. The method of claim 1, wherein the flood exposure profile comprises a substantially uniform dose profile.

4. The method of claim 1, wherein the flood exposure profile has a nonuniformity of less than about 2%.

5. The method of claim 1, wherein the flood exposure profile comprises a nonuniform dose profile selected to compensate for non-uniformity in a prior or a subsequent substrate processing step, or both.

6. The method of claim 1, wherein the source comprises a single light source.

7. The method of claim 1, wherein the source comprises multiple light sources.

8. The method of claim 1, wherein the source comprises an ultraviolet (UV) source.

9. The method of claim 8, wherein the UV source comprises a microwave UV lamp, a UV light-emitting diode (LED), a UV LED array, or a UV laser.

10. The method of claim 1, wherein controlling at least one parameter selected from a group consisting of the substrate rotation rate, the source scanning rate, the substrate scanning rate, the source power setting, the distance from the source to the substrate, the source aperture setting, the angle of incidence of flood irradiation on the substrate, and the source focus position compensates for spatial non-uniformity of the source or temporal non-uniformity of the source, or both.

11. The method of claim 1, further comprising:
measuring the flood irradiation from the source using a photosensor; and
controlling at least one parameter selected from a group consisting of the substrate rotation rate, the source scanning rate, the substrate scanning rate, the source power setting, the distance from the source to the substrate, the source aperture setting, the angle of incidence of flood irradiation on the substrate, and the source focus position to compensate for measured spatial UV flood irradiation non-uniformity or measured temporal flood exposure non-uniformity, or both.

12. The method of claim 11, wherein the photosensor is mounted on the substrate holder, adjacent the periphery of the substrate.

13. The method of claim 11, wherein the photosensor can be scanned along the source.

14. The method of claim 11, wherein the flood exposure treatment system comprises a plurality of photosensors.

15. The method of claim 11, wherein the photosensor comprises a photodiode.

16. An apparatus comprising:
at least one photosensor configured to measure flood irradiation from a source;
at least one homogenization circuit configured to determine, based on the measured flood irradiation, at least one parameter selected from a group consisting of a substrate rotation rate, the source scanning rate, the substrate scanning rate, the source power setting, a distance from the source to the substrate, the source aperture setting, an angle of incidence of flood irradiation on the substrate, and the source focus position; and
at least one control circuit configured to control substrate processing using the at least one parameter to compensate for measured spatial flood irradiation non-uniformity or measured temporal flood exposure non-uniformity, or both.

17. The apparatus of claim 16, wherein the at least one photosensor is mounted on the substrate holder, adjacent the periphery of the substrate.

18. The apparatus of claim 16, wherein the at least one photosensor can be scanned along the UV source.

19. The apparatus of claim 16, wherein the at least one photosensor comprises a photodiode.

20. The apparatus of claim 16, wherein the source comprises an ultraviolet (UV) source.

* * * * *